United States Patent [19]

Pernot

[11] Patent Number: 4,693,685
[45] Date of Patent: Sep. 15, 1987

[54] GEAR RATIO STEP-DOWN OR STEP-UP DEVICE FOR DENTAL HANDPIECE

[75] Inventor: Jacques Pernot, Geneuille, France

[73] Assignee: Micro-Mega S.A., Besancon, France

[21] Appl. No.: 795,999

[22] Filed: Nov. 7, 1985

[30] Foreign Application Priority Data

Nov. 7, 1984 [FR] France ................... 84 17335

[51] Int. Cl.[4] ................................. A61C 1/08
[52] U.S. Cl. ..................................... 433/105
[58] Field of Search ........................... 433/105

[56] References Cited

U.S. PATENT DOCUMENTS

| | | | |
|---|---|---|---|
| 3,229,369 | 1/1966 | Hoffmeister et al. | 433/105 |
| 4,278,428 | 7/1981 | Straihammer et al. | 433/105 |
| 4,475,889 | 10/1984 | Garcia et al. | 433/105 |

FOREIGN PATENT DOCUMENTS 3036939  6/1981  Fed. Rep. of Germany ...... 433/105

Primary Examiner—John J. Wilson

[57] ABSTRACT

A transmission device for use in a dental handpiece has a modular unit comprising an input shaft coaxial to and driven by the motor shaft, and an oblique shaft extending obliquely with respect to the input shaft and also to the tool driving shaft. Each end of the oblique shaft carries a bevel pinion, one bevel pinion meshing with a bevel wheel fixed to the input shaft and the other bevel pinion meshes with another bevel wheel fixed to the tool driving shaft. The input and oblique shafts are mounted in suitable bores formed in a socket, the oblique bore remaining without the peripheral limits of the socket. The socket is adapted to be forcibly fitted into the handle of the handpiece.

12 Claims, 3 Drawing Figures

GEAR RATIO STEP-DOWN OR STEP-UP DEVICE FOR DENTAL HANDPIECE

BACKGROUND OF THE INVENTION

The present invention relates to a gear ratio step-down or step-up adjusting device or transmission device for a dental handpiece, this device being adapted to be mounted between a tool driving shaft and a motor output shaft.

THE PRIOR ART

Dental operations requiring the rotation of instruments or tools for burring, boring, drilling, filling and the like are carried out at speeds in the range of about 600 r.p.m. to about 150,000 r.p.m. The rotational velocity of driving motors varies from about 4,000 to about 40,000 r.p.m. Therefore, it is necessary to provide some means for either reducing or multiplying the motor speed. In a co-pending patent application, the Applicant already proposed a handpiece adapted to be operated with interchangeable gear ratio step-down or step-up devices.

SUMMARY OF THE INVENTION

It is the primary object of the present invention to provide a particularly compact yet reliable step-down or step-up device of this feature, which has reduced overall dimensions and is adapted to be easily fitted into the handle of a handpiece.

For this purpose, the gear ratio step-down or step-up device according to the present invention is characterised by the fact that it constitutes a modular or standard unit and comprises an input shaft coaxial to and driven by the motor shaft, and another shaft extending obliquely relative to said input shaft and to the tool driving shaft, said oblique shaft carrying at each end a bevel pinion, a first bevel pinion meshing with a bevel wheel fixed to the input shaft, the second bevel pinion meshing with a bevel wheel fixed to the tool driving shaft. The input shaft is journaled in an axial bore of a socket and the oblique shaft is journaled in an oblique bore formed through said socket while intersecting said axial bore without projecting beyond the outer peripheral contour of said socket, the socket being adapted to be forcibly fitted into the handle of said handpiece.

The main advantageous features obtained with this device are derived mainly from its modular configuration affording a substantial simplification in its manufacture. In fact, while utilizing the same basic component elements, it is only necessary to select bevel pinions defining the desired gear ratios for obtaining a step-down device or a step-up device.

Moreover, this unit is intended for fitting interchangeably in the dental handpiece so that it can be replaced by another modular unit having a different gear ratio, as described in the above-mentioned co-pending patent application.

Other advantages will appear as the following description proceeds with reference to the accompanying drawings illustrating diagrammatically an exemplary form of an embodiment of the step-down or step-up device of the invention.

THE DRAWINGS

FIG. 1 is a longitudinal axial section showing in a large scale the essential component elements of the device, FIG. 2 is a diagrammatic view showing a contra-angle handpiece equipped with the step-up device of FIG. 1, and FIG. 3 is a view similar to FIG. 2 but showing a straight handpiece equipped with the step-up device of FIG. 1.

DESCRIPTION OF THE PREFERRED EMBODIMENT

Figure 1:
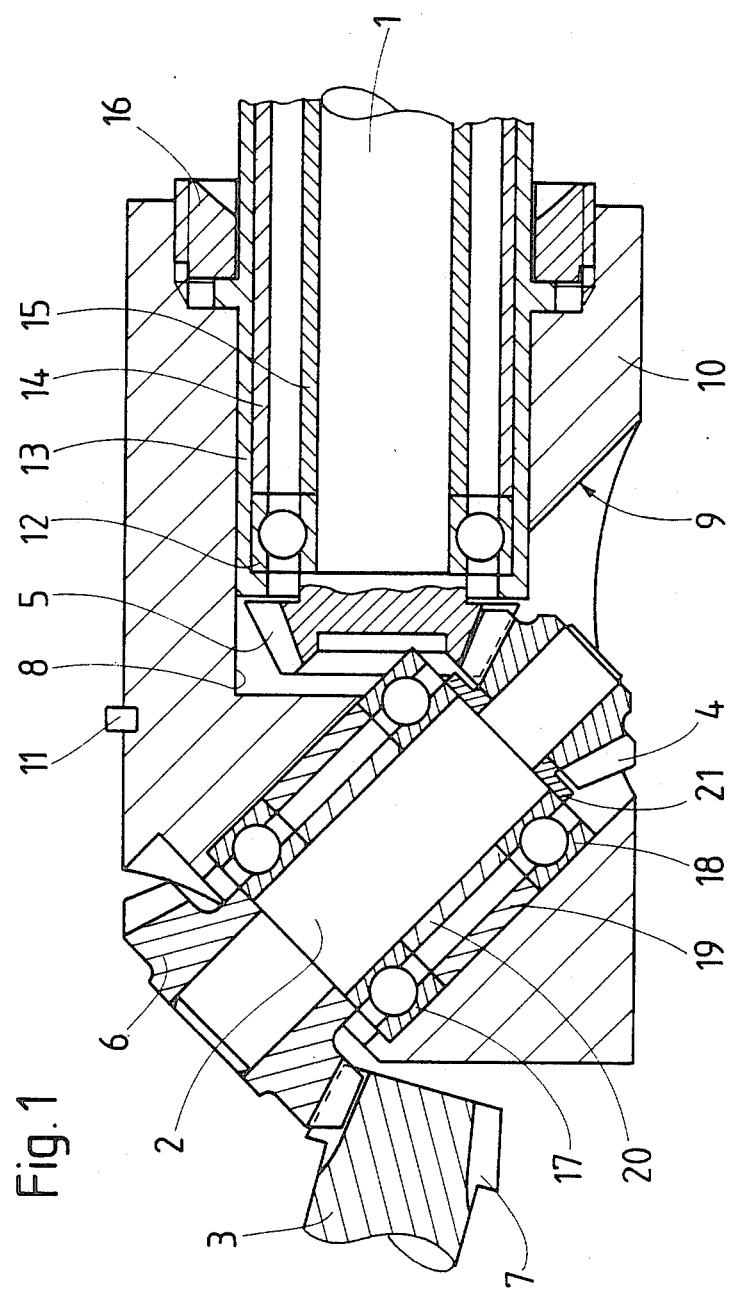

The device shown in a longitudinal axial section in FIG. 1 comprises an input shaft 1 coaxial with the motor shaft (not shown) and driven by the motor through known means, and an intermediate oblique shaft 2 extending at an angle with respect to the input shaft 1 and also to the tool driving output shaft 3. The intermediate oblique shaft 2 is provided at each end with a bevel pinion, one pinion 4 meshing with a bevel wheel 5 fixed to the input shaft 1, the other pinion 6 meshing with another bevel wheel 7 fixed to the tool driving shaft 3. The input and oblique shafts 1, 2 are rotatably mounted respectively in an axial bore 8 and in an oblique bore 9 formed in a socket 10 adapted to be fitted into the handle of the handpiece. This socket 10 further comprises means for positioning the handpiece, which consists, for example, of a key 11 adapted to engage with a longitudinal slot formed in the handpiece handle, as described, for example, in a copending patent application filed by the same Applicant. The oblique through bore 9 intersects the axial bore 8 and terminates at opposite peripheral sides of the socket 10, thus facilitating the assembling of the various component elements. The oblique shaft 9 does not projects beyond the outer peripheral surface of the socket 10.

The input shaft 1 is supported in the axial bore 8 of socket 10 by a pair of bearings, preferably ball-bearings, of which only one bearing 12 is shown in FIG. 1, said bearings being housed in a ball-bearing shell 13 acting as a stop member, the outer and inner races of the bearings being separated by cylindrical distance-pieces 14,15. The shaft 1 is held in an axial position by a lock ring 16, forcibly fitted in the socket 10.

The oblique shaft 2 is supported by a pair of bearings 17,18 also of the ball-bearing type inserted in the oblique bore 9 and held at the proper axial distance by a pair of cylindrical distance-pieces or spacers 19,20. The first distance-piece 19 is forcibly fitted in the oblique bore and holds in position the assembly comprising the shaft 2, ball-bearings 17,18 and bevel pinion 4. A ring 21 forcibly fitted on the end of the oblique shaft 2 is provided for holding ball-bearing 18 in the proper axial position. In a modified form of embodiment, the assembly comprising the shaft 2, ball-bearings 17,18 and distance-pieces 19,20 may be housed in a socket provided with a notch engageable with a tapped plate secured in turn by a screw. By turning this screw the oblique shaft can be locked tightly in its recess. Other means for fixing the oblique shaft may be contemplated without departing from the basic principles of the invention.

According to the diameters of the bevel pinions, the gear ratio may be either reduced or multiplied, as required.

Figure 2:
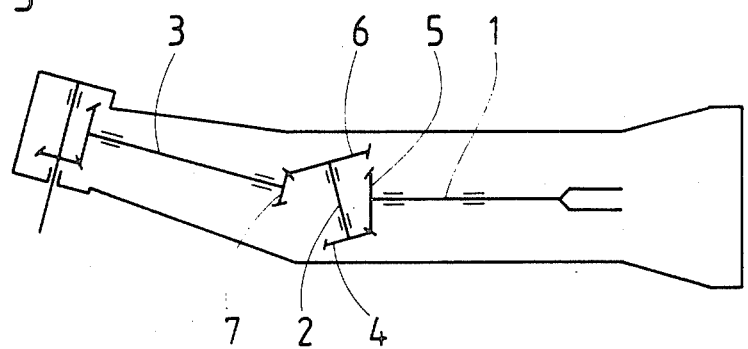
Figure 3:
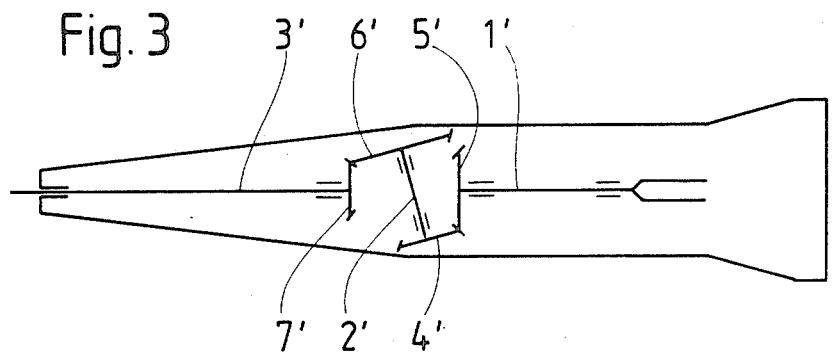

This gear ratio step-down or step-up device may be used either in a contra-angle as shown diagrammatically in FIG. 2, or in a straight handpiece as shown also diagrammatically in FIG. 3. In the first instance, the tool driving shaft 3 is disposed within a front portion of the longitudinal body of the handpiece and set at an angle of about 15 degrees relative to the handle and the oblique front section of the longitudinal body of the handpiece is detachable. In the second case, the longitudinal body of the handpiece is a one-piece structure and the tool driving shaft 3' is coaxial to the input shaft 1'. In this case, the assembly comprises the same driving members 2' to 7' consistent with this type of straight handpiece configuration.

The above-described device constructed in the form of a modular or standard unit can therefore be easily and detachably mounted in the handle of a handpiece such as disclosed in the co-pending U.S. patent application Ser. No. 795,998, and this handpiece may also receive different modular units to provide different gear ratios. The above-described modular unit as well as the various other modular units are provided with an input shaft adapted to be coupled directly to the output shaft of the driving motor when this motor is fitted into the rear end of the handle.

What is claimed is:

1. A gear-ratio adjusting device of a dental handpiece which is mounted between a tool driving shaft having a bevel wheel at one end thereof and a motor shaft, said device having a modular unit structure and comprising: a socket forcibly fitted into a handle of the dental handpiece, said socket having means defining an axial bore longitudinally extending in the socket, and means defining an oblique through-bore extending obliquely relative to the axial bore in the socket and being open at the periphery of the socket; and input shaft coaxial with and driven by said motor shaft and having a bevel wheel at one end thereof; and an oblique shaft inclined relative to said input shaft and to the tool driving shaft, said oblique shaft being provided at the ends thereof with a pair of bevel pinions meshing with the bevel wheel fixed to said input shaft and with the bevel wheel fixed to the tool driving shaft respectively, said input shaft being rotatably mounted in the axial bore of the socket, said oblique shaft being rotatably mounted in the oblique through-bore formed in said socket.

2. The device according to claim 1; including a pair of bearings inserted in said oblique through-bore for supporting the oblique shaft and a cylindrical distance-piece disposed between the pair of bearings for axially spacing the same.

3. A transmission device of a dental handpiece for transmitting rotation of a motor shaft to a tool at a certain gear ratio, the transmission device comprising: a longitudinal body having front and rear portions and having means defining an oblique bore therein extending obliquely relative to the longitudinal axis of the body and opening at a peripheral portion of the body; an input shaft rotatably mounted within the rear portion of the body and connectable to a motor shaft to be rotationally driven thereby during use of the transmission device, the input shaft extending longitudinally rearwardly from the oblique bore and having a bevel wheel at the front end thereof; an output shaft rotatably mounted within the front portion of the body and connectable to a tool to rotationally drive the tool during use of the transmission device, the output shaft extending longitudinally forwardly from the oblique bore and having a bevel wheel at the rear end thereof; and an intermediate shaft rotatably and replaceably inserted into the oblique bore through the peripheral opening, the intermediate shaft having at opposite ends thereof a pair of bevel pinions engageable with respective ones of the bevel wheels of the input and output shafts when the intermediate shaft is inserted into the oblique bore.

4. A transmission device according to claim 3; wherein the oblique bore comprises an oblique through-bore.

5. A transmission device according to claim 3; including bearing means disposed within the oblique bore for rotatably supporting the intermediate shaft.

6. A transmission device according to claim 5; wherein the bearing means comprises a pair of axially spaced bearings, and a cylindrical spacer disposed therebetween.

7. A transmission device according to claim 3; wherein the body has means therein defining an axial bore longitudinally extending in the rear portion of the body for replaceably receiving therein an input shaft.

8. A transmission device according to claim 3; wherein the bevel pinions and wheels are selected from a group of different bevel pinions and wheels to define one of a plurality of different reduction gear-ratios of the transmission device.

9. A transmission device according to claim 3; wherein the bevel pinions and wheels are selected from a group of different bevel pinions and wheels to define one of a plurality of different multiplying gear-ratios of the transmission device.

10. A transmission device according to claim 3; wherein the front and rear body portions are inclined with respect to each other.

11. A transmission device according to claim 3; wherein the front and rear body portions are linearly aligned with each other.

12. A transmission device according to claim 11; wherein the body has one-piece structure.

* * * * *